(12) United States Patent
Garrison

(10) Patent No.: US 10,441,351 B2
(45) Date of Patent: *Oct. 15, 2019

(54) ELECTRICALLY-INSULATIVE HINGE FOR ELECTROSURGICAL JAW ASSEMBLY, BIPOLAR FORCEPS INCLUDING SAME, AND METHODS OF JAW-ASSEMBLY ALIGNMENT USING FASTENED ELECTRICALLY-INSULATIVE HINGE

(71) Applicant: COVIDIEN LP, Mansfield, MA (US)

(72) Inventor: David M. Garrison, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 451 days.

This patent is subject to a terminal disclaimer.

(21) Appl. No.: 15/189,338

(22) Filed: Jun. 22, 2016

(65) Prior Publication Data

US 2016/0302849 A1 Oct. 20, 2016

Related U.S. Application Data

(63) Continuation of application No. 13/080,383, filed on Apr. 5, 2011, now Pat. No. 9,381,059.

(51) Int. Cl.
*A61B 18/14* (2006.01)
*A61B 17/28* (2006.01)
(Continued)

(52) U.S. Cl.
CPC ........ *A61B 18/1445* (2013.01); *A61B 17/282* (2013.01); *A61B 17/2812* (2013.01);
(Continued)

(58) Field of Classification Search
CPC ............ A61B 18/1442; A61B 18/1445; A61B 18/1447; A61B 2018/145;
(Continued)

(56) References Cited

U.S. PATENT DOCUMENTS

D223,367 S 4/1972 Kountz
D263,020 S 2/1982 Rau, III
(Continued)

FOREIGN PATENT DOCUMENTS

CN 1103807 A 6/1995
DE 390937 C 3/1924
(Continued)

OTHER PUBLICATIONS

Walt Boyles, "Instrumentation Reference Book", 2002, Butterworth-Heinemann, pp. 262-264.
(Continued)

*Primary Examiner* — Ronald Hupczey, Jr.

(57) ABSTRACT

An end effector assembly suitable for use with a forceps includes opposing first and second jaw members pivotably mounted with respect to one another. The first jaw member includes one or more pivot holes defined therein configured to receive a portion of a pivot pin therein. The end effector assembly also includes an electrically-insulative hinge configured to electrically isolate the first and second jaw members from one another including one or more pivot-hole locators having an aperture defined therein. The electrically-insulative hinge is attached to the first jaw member such that the one or more pivot-hole locators align with the one or more pivot holes of the second jaw member.

20 Claims, 12 Drawing Sheets

(51) Int. Cl.
*A61B 17/29* (2006.01)
*A61B 18/00* (2006.01)

(52) U.S. Cl.
CPC ...... *A61B 17/2816* (2013.01); *A61B 18/1442* (2013.01); *A61B 2017/2919* (2013.01); *A61B 2017/2939* (2013.01); *A61B 2017/2947* (2013.01); *A61B 2018/0063* (2013.01); *A61B 2018/00083* (2013.01); *A61B 2018/145* (2013.01); *A61B 2018/1455* (2013.01)

(58) Field of Classification Search
CPC .... A61B 2018/1452; A61B 2018/1455; A61B 2018/1457; A61B 2017/2926; A61B 2017/2939; A61B 2017/2947
See application file for complete search history.

(56) References Cited

U.S. PATENT DOCUMENTS

| | | |
|---|---|---|
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| D354,218 S | 1/1995 | Van de Peer |
| 5,637,110 A * | 6/1997 | Pennybacker ..... A61B 18/1445 606/170 |
| 5,853,412 A | 12/1998 | Mayenberger |
| 6,010,516 A | 1/2000 | Hulka |
| D424,693 S | 5/2000 | Pruter |
| D424,694 S | 5/2000 | Tetzlaff et al. |
| D425,201 S | 5/2000 | Tetzlaff et al. |
| 6,096,037 A | 8/2000 | Mulier et al. |
| 6,238,414 B1 | 5/2001 | Griffiths |
| D449,886 S | 10/2001 | Tetzlaff et al. |
| D457,958 S | 5/2002 | Dycus et al. |
| D457,959 S | 5/2002 | Tetzlaff et al. |
| 6,669,696 B2 | 12/2003 | Bacher et al. |
| D487,039 S | 2/2004 | Webster et al. |
| D496,997 S | 10/2004 | Dycus et al. |
| 6,808,491 B2 | 10/2004 | Kortenbach et al. |
| D499,181 S | 11/2004 | Dycus et al. |
| 6,905,497 B2 | 6/2005 | Truckai et al. |
| D525,361 S | 7/2006 | Hushka |
| 7,103,947 B2 | 9/2006 | Sartor et al. |
| D531,311 S | 10/2006 | Guerra et al. |
| D533,942 S | 12/2006 | Kerr et al. |
| 7,150,097 B2 | 12/2006 | Sremcich et al. |
| 7,150,749 B2 | 12/2006 | Dycus et al. |
| D535,027 S | 1/2007 | James et al. |
| 7,156,846 B2 | 1/2007 | Dycus et al. |
| D541,418 S | 4/2007 | Schechter et al. |
| 7,204,835 B2 | 4/2007 | Latterell et al. |
| D541,938 S | 5/2007 | Kerr et al. |
| D564,662 S | 3/2008 | Moses et al. |
| D576,932 S | 9/2008 | Strehler |
| 7,510,556 B2 * | 3/2009 | Nguyen ............. A61B 18/1445 606/51 |
| D594,736 S | 6/2009 | Esjunin |
| D594,737 S | 6/2009 | Kelly et al. |
| 7,540,872 B2 | 6/2009 | Schechter et al. |
| 7,553,311 B2 | 6/2009 | Anders et al. |
| 7,566,334 B2 | 7/2009 | Christian et al. |
| 7,597,693 B2 | 10/2009 | Garrison |
| D606,203 S | 12/2009 | Husheer et al. |
| D613,412 S | 4/2010 | DeCarlo |
| 7,776,065 B2 | 8/2010 | Griffiths et al. |
| D634,010 S | 3/2011 | DeCarlo |
| 8,454,601 B2 | 6/2013 | Sutter et al. |
| 8,647,341 B2 | 2/2014 | Dycus et al. |
| 9,381,059 B2 * | 7/2016 | Garrison ............ A61B 18/1445 |
| 2002/0019632 A1 | 2/2002 | Mayenberger |
| 2002/0128649 A1 | 9/2002 | Bacher et al. |
| 2002/0183784 A1 | 12/2002 | Lutze et al. |
| 2002/0188294 A1 | 12/2002 | Couture et al. |
| 2003/0216733 A1 | 11/2003 | McClurken et al. |
| 2004/0193153 A1 | 9/2004 | Sartor et al. |
| 2004/0250419 A1 | 12/2004 | Sremcich et al. |
| 2005/0222602 A1 | 10/2005 | Sutter et al. |
| 2006/0264922 A1 | 11/2006 | Sartor et al. |
| 2007/0043352 A1 | 2/2007 | Garrison et al. |
| 2007/0078458 A1 | 4/2007 | Dumbauld et al. |
| 2007/0078459 A1 | 4/2007 | Johnson et al. |
| 2007/0213712 A1 | 9/2007 | Buysse et al. |
| 2007/0299439 A1 | 12/2007 | Latterell et al. |
| 2008/0058802 A1 | 3/2008 | Couture et al. |
| 2008/0234725 A1 * | 9/2008 | Griffiths ................ A61B 17/29 606/208 |
| 2008/0243120 A1 | 10/2008 | Lawes et al. |
| 2009/0018535 A1 | 1/2009 | Schechter et al. |
| 2009/0048596 A1 | 2/2009 | Shields et al. |
| 2009/0171350 A1 | 7/2009 | Dycus et al. |
| 2009/0248052 A1 | 10/2009 | Cunningham et al. |
| 2010/0076430 A1 | 3/2010 | Romero |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 4303882 A1 | 8/1994 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1159926 A2 | 12/2001 |
| FR | 179607 | 11/1906 |
| FR | 1275415 A | 11/1961 |
| FR | 1347865 A | 1/1964 |
| FR | 2235669 A1 | 1/1975 |
| FR | 2276027 A1 | 1/1976 |
| FR | 2313708 A1 | 12/1976 |
| FR | 2502935 A1 | 10/1982 |

(56) References Cited

FOREIGN PATENT DOCUMENTS

| | | |
|---|---|---|
| FR | 2517953 A1 | 6/1983 |
| FR | 2573301 A1 | 5/1986 |
| FR | 2862813 A1 | 5/2005 |
| FR | 2864439 A1 | 7/2005 |
| JP | 55106 | 1/1993 |
| JP | 0540112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 2010035831 A1 | 4/2010 |

OTHER PUBLICATIONS

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
Search Report EP 06008779.8 dated Jul. 13, 2006.
Search Report EP 06009435 dated Jul. 13, 2006.
Search Report EP 06010499.9 dated Jan. 29, 2008.
Search Report EP 06014461.5 dated Oct. 31, 2006.
Search Report EP 06018206.0 dated Oct. 20, 2006.
Search Report EP 06019768 dated Jan. 17, 2007.
Search Report EP 06020574.7 dated Oct. 2, 2007.
Search Report EP 06020583.8 dated Feb. 7, 2007.
Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.

(56) References Cited

OTHER PUBLICATIONS

Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
Search Report EP 08007924.7 partial dated Aug. 17, 2010.
Search Report EP 08011282 dated Aug. 14, 2009.
Search Report EP 08011705 dated Aug. 20, 2009.
Search Report EP 08011705.4 extended dated Nov. 4, 2009.
Search Report EP 08012829.1 dated Oct. 29, 2008.
Search Report EP 08015842 dated Dec. 5, 2008.
Search Report EP 08019920.1 dated Mar. 27, 2009.
Search Report EP 08020530.5 dated May 27, 2009.
Search Report EP 08169973.8 dated Apr. 6, 2009.

(56) References Cited

OTHER PUBLICATIONS

European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.

(56) References Cited

OTHER PUBLICATIONS

Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T.Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis.TM. Technology (Date Unknown). "Overcoming the Challenge" located at: <http://www.urologix.com/medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3(1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.

* cited by examiner

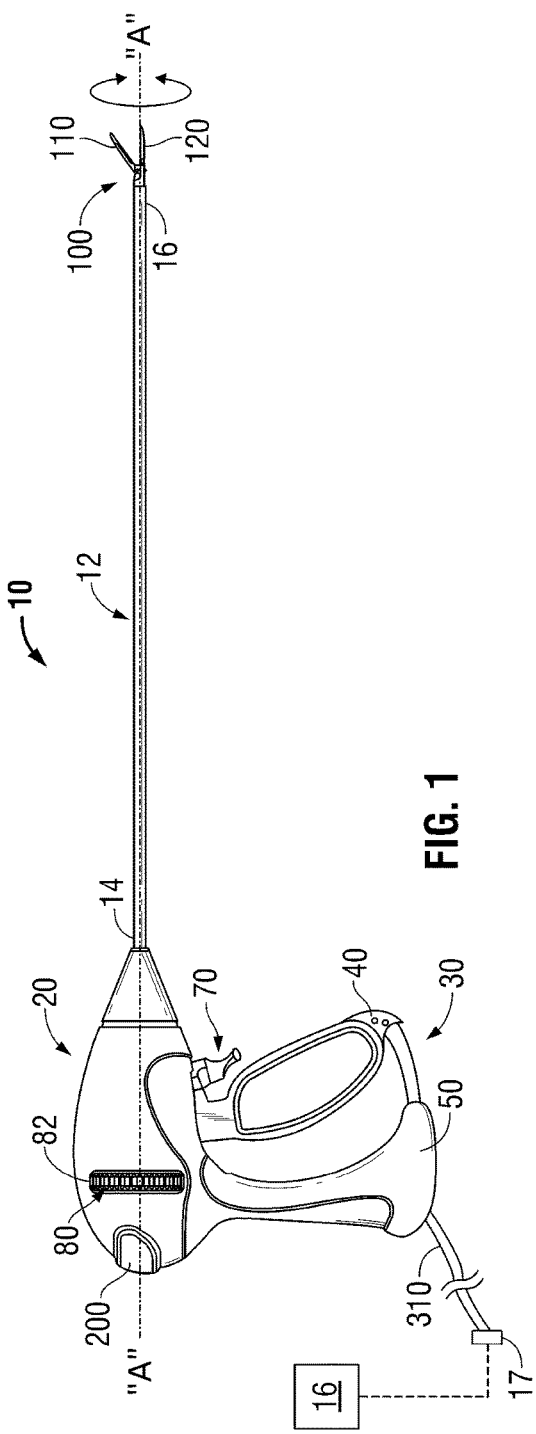
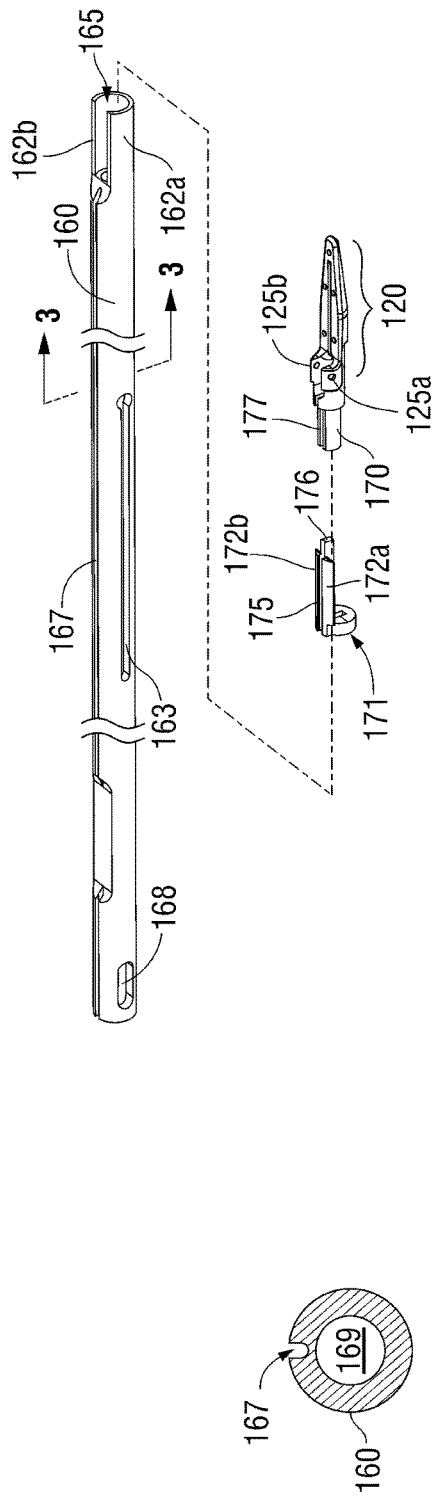
FIG. 1
FIG. 2
FIG. 3

ELECTRICALLY-INSULATIVE HINGE FOR ELECTROSURGICAL JAW ASSEMBLY, BIPOLAR FORCEPS INCLUDING SAME, AND METHODS OF JAW-ASSEMBLY ALIGNMENT USING FASTENED ELECTRICALLY-INSULATIVE HINGE

CROSS-REFERENCE TO RELATED APPLICATION

This application is a continuation of U.S. patent application Ser. No. 13/080,383, filed Apr. 5, 2011, the entire contents of which is hereby incorporated by reference.

BACKGROUND

1. Technical Field

The present disclosure relates to joints and hinges used to connect movable components of an electrosurgical instrument and, more particularly, to an electrically-insulative hinge for use in an electrosurgical jaw assembly, a bipolar forceps including an electrically-insulative hinge, and methods of jaw-assembly alignment using a fastened electrically-insulative hinge.

2. Discussion of Related Art

Electrosurgical instruments, such as electrosurgical forceps, have become widely used by surgeons. Electrosurgery involves application of high-frequency electrical current to a surgical site to cut, ablate, coagulate, cauterize or seal tissue.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode.

In bipolar electrosurgery, the electrosurgical device includes two electrodes that are located in proximity to one another for the application of current between their surfaces. Bipolar electrosurgical current travels from one electrode, through the intervening tissue to the other electrode to complete the electrical circuit. Bipolar instruments generally include end effectors, such as grippers, cutters, forceps, dissectors and the like.

Bipolar electrosurgical forceps utilize two generally opposing electrodes that are operably associated with the inner opposing surfaces of end effectors and that are both electrically coupled to an electrosurgical generator. Each electrode is charged to a different electric potential. By utilizing an electrosurgical forceps, a surgeon can utilize both clamping action and electrosurgical energy to cauterize, coagulate/desiccate and/or cut tissue and/or simply reduce or slow bleeding by controlling the intensity, frequency and duration of the electrosurgical energy applied to the tissue.

Typically, joints and hinges for use in electrosurgical instruments to connect movable components are formed from an electrically-insulative material to prevent electrical shorting between component parts and/or prevent the formation of alternate current paths through the instrument. As such, instrument designers have manufactured electrosurgical instruments that involve complex, rotating hinge configurations to isolate, insulate and/or control the electrosurgical active areas of the instrument.

Traditional metal hinge configurations generally include multiple, independent sub-assemblies. Typically, the sub-assemblies are overmolded with plastic material having high bond strength. These separately overmolded sub-assemblies are mechanically integrated and arranged in a series of manufacturing steps that often require tightly controlled, time-consuming processes to achieve proper jaw alignment. Additional steps are often undertaken to control other parameters associated with the rotational movement about the hinge, e.g., friction, torque, etc.

SUMMARY

A continuing need exists for a simple and effective electrically-insulative hinge that can be readily integrated into the manufacturing process to electrically isolate the movable components of an electrosurgical instrument. Further need exists for the development of a manufacturing process that effectively fabricates an electrosurgical instrument including an electrically-insulative hinge that electrically isolates and structurally integrates the electrically-active components of the instrument and results in the formation of a reliable instrument that meets specific tolerance requirements for proper jaw alignment and/or gap distances.

The present disclosure relates to an end effector assembly suitable for use with a forceps. The end effector assembly includes opposing first and second jaw members pivotably mounted with respect to one another. The first jaw member includes one or more pivot holes defined therein configured to receive a portion of a pivot pin therein. The end effector assembly also includes an electrically-insulative hinge configured to electrically isolate the first and second jaw members from one another including one or more pivot-hole locators defined therein. The electrically-insulative hinge is attached to the second jaw member such that the one or more pivot-hole locators aligns with the one or more pivot holes defined in the first jaw member.

The present disclosure also relates to a bipolar forceps including a housing, a shaft extending from the housing and including a distal end configured to support an end effector assembly. The end effector assembly includes opposing jaw members pivotably mounted with respect to one another, each of the jaw members including a sealing surface associated therewith. The jaw members are moveable from a first position in spaced relation relative to one another to one or more subsequent positions wherein the sealing surfaces cooperate to grasp tissue therebetween. The end effector assembly also includes an electrically-insulative hinge configured to electrically isolate the jaw members from one another including one or more pivot-hole locators each having an aperture defined therein. The electrically-insulative hinge is attached to one of the jaw members such that the aperture of each of the one or more pivot-hole locators aligns with a pivot hole defined in the opposing jaw member, wherein the electrically-insulative hinge is configured to electrically isolate the jaw members from one another.

The present disclosure also relates to a method of manufacturing an end effector assembly including the initial steps of providing a first jaw member and providing a second jaw member including one or more pivot holes defined therethrough. The method also includes the steps of providing an electrically-insulative hinge including one or more pivot-hole locators defined therein, attaching the electrically-insulative hinge to the first jaw member such that the one or more pivot-hole locators align with the one or more pivot holes of the second jaw member, and pinning the first and second jaw members via the one or more pivot-hole locators and the one or more pivot holes such that the first and second jaw members are pivotably mounted with respect to one another.

The present disclosure also relates to a method of manufacturing an end effector assembly including the initial steps of providing a first jaw member including a first pivot hole defined therethrough and providing a second jaw member including a second pivot hole defined therethrough. The method also includes the steps of providing an electrically-insulative hinge including at least one pivot-hole locator defined therein, attaching the electrically-insulative hinge to the first jaw member such that the at least one pivot-hole locator aligns with the first pivot hole, providing a fixture configured to releaseably hold the first jaw member in contact with the second jaw member, providing a pivot pin, coupling the fixture to the first and second jaw members, and inserting the pivot pin through the at least one pivot-hole locator into the first and second pivot holes such that the first and second jaw members are pivotably mounted with respect to one another.

BRIEF DESCRIPTION OF THE DRAWINGS

Objects and features of the presently-disclosed electrically-insulative hinge for use in an electrosurgical jaw assembly, a bipolar forceps including an electrically-insulative hinge, and methods of jaw-assembly alignment using a fastened electrically-insulative hinge will become apparent to those of ordinary skill in the art when descriptions of various embodiments thereof are read with reference to the accompanying drawings, of which:

FIG. 1 is a left, side view of an endoscopic bipolar forceps showing a housing, a rotatable member, a shaft and an end effector assembly according to an embodiment of the present disclosure;

FIG. 2 is an enlarged, perspective view of the shaft and lower jaw member of the forceps shown in FIG. 1 with parts separated according to an embodiment of the present disclosure;

FIG. 3 is an enlarged, cross-sectional view of the indicated area of detail of FIG. 2 according to an embodiment of the present disclosure;

DETAILED DESCRIPTION

Figure 4:
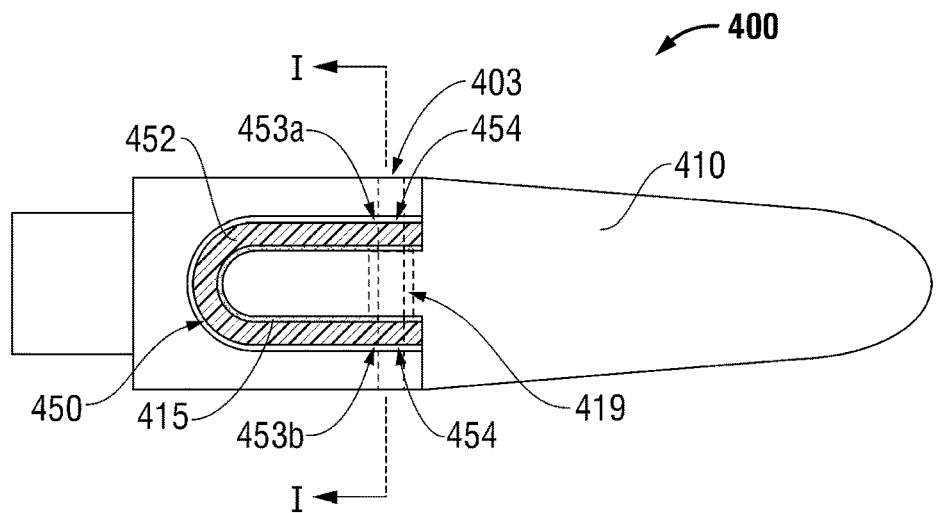
FIG. 4 is a schematic diagram of the end effector assembly with an electrically-insulative hinge according to an embodiment of the present disclosure.

Hereinafter, embodiments of an electrically-insulative hinge for use in an electrosurgical jaw assembly, a bipolar forceps including an electrically-insulative hinge, and methods of jaw-assembly alignment using a fastened electrically-insulative hinge of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as, for example, microwave ablation, radiofrequency (RF) ablation, or microwave or RF ablation-assisted resection. As it is used in this description, "transmission line" generally refers to any transmission medium that can be used for the propagation of signals from one point to another.

Various embodiments of the present disclosure provide a bipolar forceps with an end effector assembly including opposing jaw members pivotably mounted with respect to one another, and an electrically-insulative hinge fastened to one of the jaw members, wherein the electrically-insulative hinge is configured to electrically isolate the jaw members from one another. Various embodiments of the present disclosure provide methods of manufacturing an end effector assembly including the presently-disclosed electrically-insulative hinge.

Figure 16:
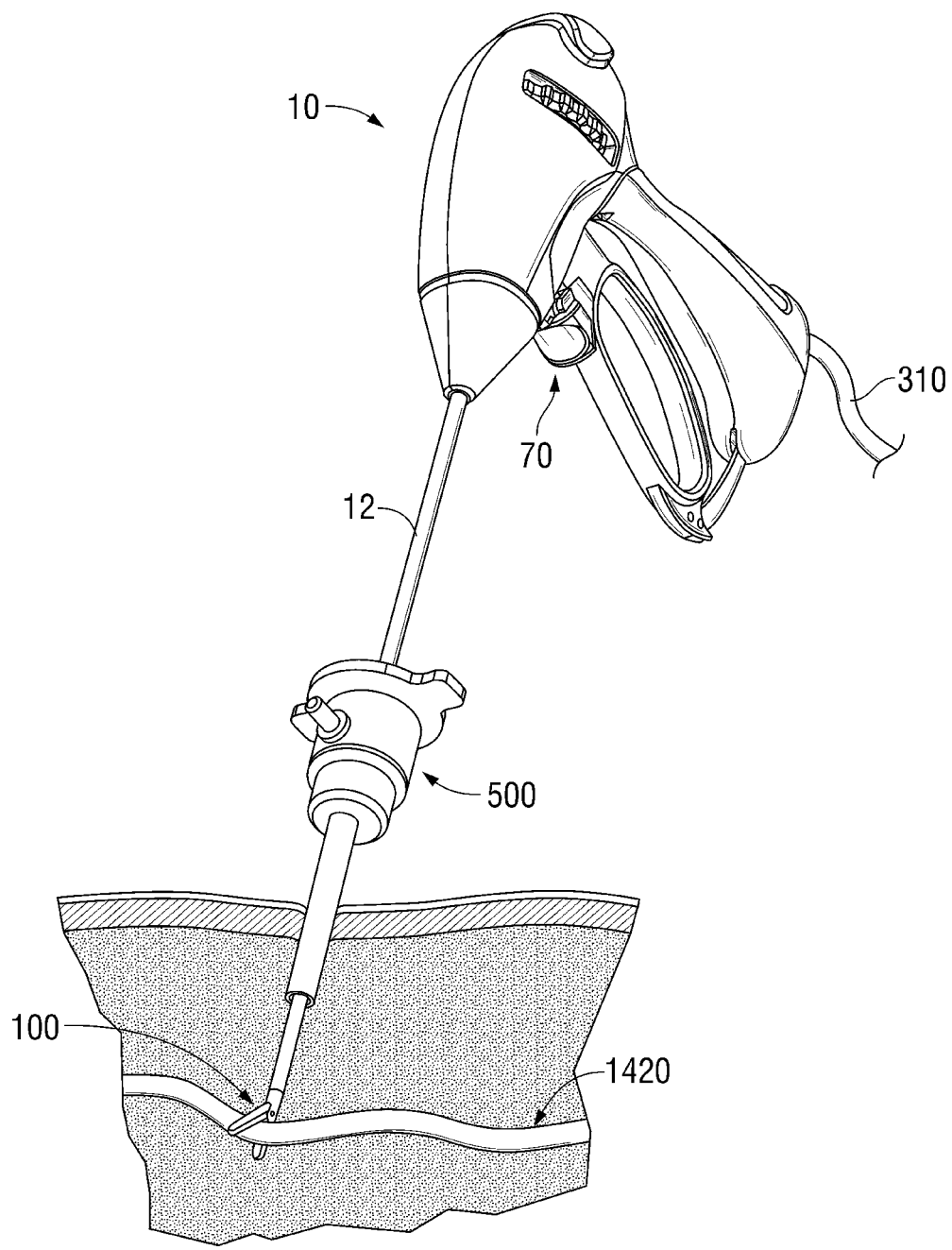
FIG. 16 is a perspective view showing the forceps of the present disclosure utilized with a cannula.

Embodiments of the presently-disclosed bipolar forceps may be suitable for utilization in endoscopic surgical procedures, such as shown in FIG. 16, and/or suitable for utilization in open surgical applications. Embodiments of the presently-disclosed bipolar forceps may be implemented using electromagnetic radiation at microwave frequencies, RF frequencies or at other frequencies. An electrosurgical system including the presently-disclosed endoscopic bipolar forceps operatively coupled to an electrosurgical energy source (e.g., 16 shown in FIG. 1) according to various embodiments is designed and configured to operate at frequencies between about 300 KHz and about 10 GHz.

Although the following description describes the use of an endoscopic bipolar forceps, the teachings of the present disclosure may also apply to a variety of electrosurgical devices that include hinges used to connect movable components thereof.

Figure 14:
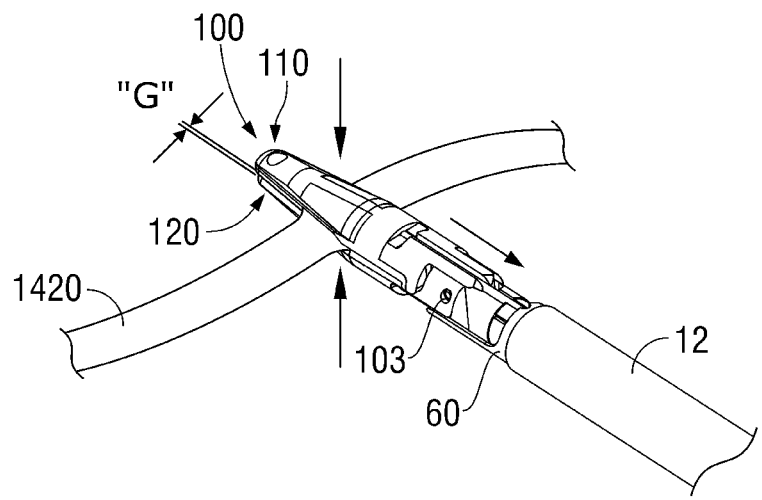
FIG. 14 is an enlarged, rear perspective view of the end effector assembly of FIG. 1 shown grasping tissue.
Figure 15:
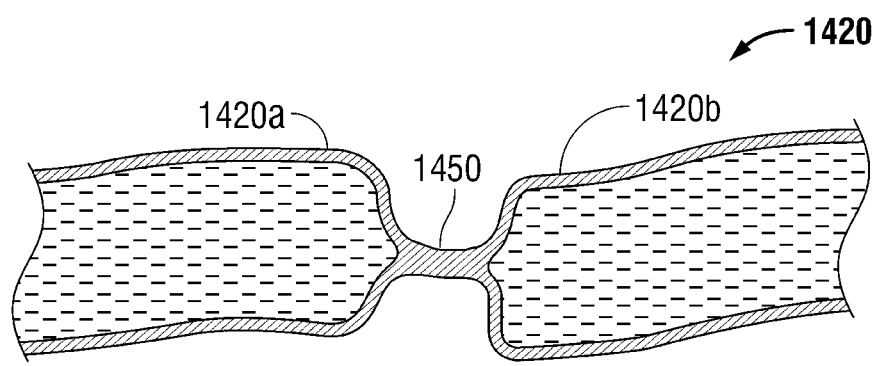
FIG. 15 is an enlarged, cross-sectional view of a tissue seal.

In FIG. 1, an embodiment of an endoscopic bipolar forceps 10 is shown for use with various surgical procedures and generally includes a housing 20, a handle assembly 30, a rotatable assembly 80, a trigger assembly 70 and an end effector assembly 100 that mutually cooperate to grasp, seal and/or divide tubular vessels and vascular tissue (e.g., 1420 shown in FIGS. 14 through 16). Although FIG. 1 depicts a bipolar forceps 10 for use in connection with endoscopic surgical procedures, the teachings of the present disclosure may also apply to more traditional open surgical procedures. For the purposes herein, the forceps 10 is described in terms of an endoscopic instrument; however, it is contemplated that an open version of the forceps may also include the same or similar operating components and features as described below.

Forceps 10 includes a shaft 12 that has a distal end 16 configured to mechanically engage the end effector assembly 100 and a proximal end 14 configured to mechanically engage the housing 20. In some embodiments, the shaft 12 has a length from a proximal side of the handle assembly 30 to a distal side of the forceps 10 in a range of about 7 centimeters to about 44 centimeters.

Details of how the shaft 12 connects to the end effector assembly 100 are described in more detail below with respect to FIG. 2. The proximal end 14 of the shaft 12 is received within the housing 20, and connections relating thereto are disclosed in commonly assigned U.S. Pat. No. 7,150,097 entitled "METHOD OF MANUFACTURING JAW ASSEMBLY FOR VESSEL SEALER AND DIVIDER", commonly assigned U.S. Pat. No. 7,156,846 entitled "VESSEL SEALER AND DIVIDER FOR USE WITH SMALL TROCARS AND CANNULAS", commonly assigned U.S. Pat. No. 7,597,693 entitled "VESSEL SEALER AND DIVIDER FOR USE WITH SMALL TROCARS AND CANNULAS" and commonly assigned U.S. Pat. No. 7,771,425 entitled "VESSEL SEALER AND DIVIDER HAVING A VARIABLE JAW CLAMPING MECHANISM".

Forceps 10 includes an electrosurgical cable 310. Electrosurgical cable 310 may be formed from a suitable flexible, semi-rigid or rigid cable, and may connect directly to an electrosurgical power generating source 16, e.g., a microwave or RF electrosurgical generator. In some embodiments, the electrosurgical cable 310 connects the forceps 10 to a connector 17, which further operably connects the instrument 10 to the electrosurgical power generating source 16. Electrosurgical cable 310 may be internally divided into one or more cable leads (e.g., 311 shown in FIG. 12) each of which transmits electrosurgical energy through their respective feed paths to the end effector assembly 100.

Electrosurgical power generating source 16 may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ™, FORCE FX™, SURGISTAT™ II, and FORCE TRIAD™ offered by Covidien. Electrosurgical cable 310 may additionally, or alternatively, provide a conduit (not shown) configured to provide coolant fluid from a coolant source (not shown) to one or more components of the forceps 10. Forceps 10 may alternatively be configured as a wireless device or battery-powered.

End effector assembly 100 may be selectively and releaseably engageable with the distal end 16 of the shaft 12, and/or the proximal end 14 of the shaft 12 may be selectively and releaseably engageable with the housing 20 and the handle assembly 30. In either of these two instances, the forceps 10 would be considered "partially disposable" or "reposable", e.g., a new or different end effector assembly 100 (or end effector assembly 100 and shaft 12) selectively replaces the old end effector assembly 100 as needed. As can be appreciated, some of the presently-disclosed electrical and/or mechanical connections may have to be altered to modify the instrument to a reposable forceps.

Figure 7:
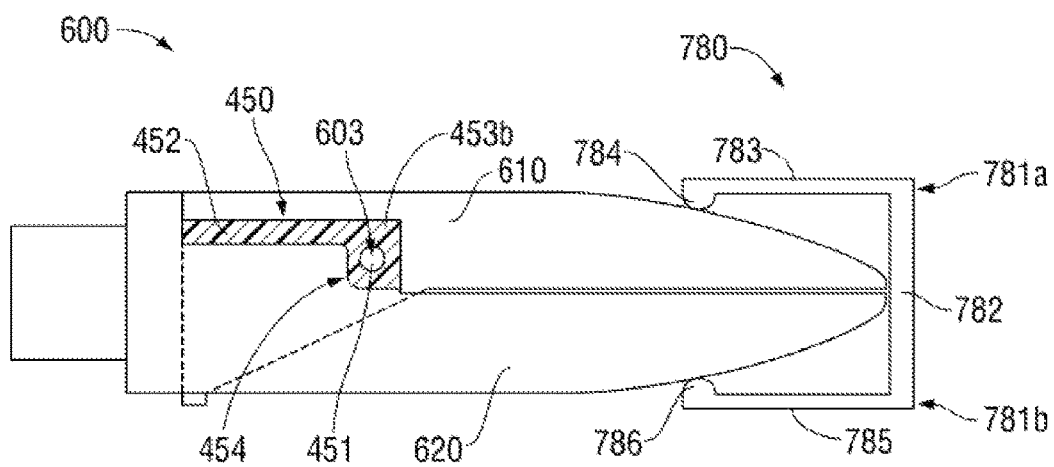
FIG. 7 is a schematic diagram showing a fixture for releaseably holding the end effector assembly of FIG. 6, such as during a fastening process, according to an embodiment of the present disclosure.

End effector assembly 100 generally includes a pair of opposing jaw members 110 and 120 pivotably mounted with respect to one another. End effector assembly 100 includes an electrically-insulative hinge 450 (shown in FIGS. 12 and 13), which is described in more detail later in this disclosure, configured to electrically isolate the jaw members from one another. Electrically-insulative hinge 450 can be used to align the jaw members 110 and 120 during assembly of the end effector assembly 100, such as shown in FIG. 7. End effector assembly 100 is designed as a unilateral assembly, i.e., the end effector assembly 100 includes a stationary or fixed jaw member 120 mounted in fixed relation to the shaft 12 and a pivoting jaw member 110 mounted about a pivot pin 103 (shown in FIGS. 10 through 13) coupled to the stationary jaw member 120. Alternatively, the forceps 10 may include a bilateral jaw assembly, i.e., both jaw members move relative to one another. A reciprocating sleeve 60 (shown in FIGS. 11 through 14) is slidingly disposed within the shaft 12. Pulling the sleeve 60 proximally closes the jaw members 110 and 120 about tissue grasped therebetween, and pushing the sleeve 60 distally opens the jaw members 110 and 120. Sleeve 60 is remotely operable by a drive assembly (not shown).

As shown in FIGS. 10 through 13, the pivoting jaw member 110 includes a detent or protrusion 117 that extends from the pivoting jaw member 110 through an aperture 62 (FIGS. 11 and 13) disposed within the reciprocating sleeve

Figure 11:
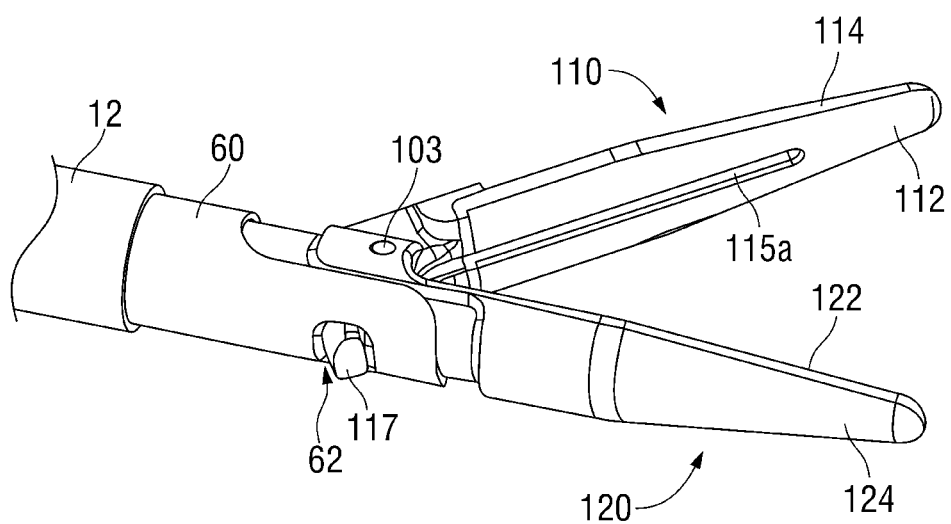
FIG. 11 is an enlarged, bottom, left perspective view of the end effector assembly of FIG. 10 according to an embodiment of the present disclosure.

60. As best shown in FIG. 11, the protrusion 117 is configured to matingly engage the aperture 62 of sleeve 60 upon retraction thereof. Pivoting jaw member 110 is actuated by sliding the reciprocating sleeve 60 axially within the shaft 12 such that a distal end of the aperture 62 abuts against the detent 117 on the pivoting jaw member 110. For example, proximal movement of the sleeve 60 engages detent 117 to pivot the jaw member 110 to a closed position for grasping purposes.

As shown in FIG. 1, the end effector assembly 100 is rotatable about a longitudinal axis "A-A" through rotation, either manually or otherwise, of the rotatable assembly 80. Rotatable assembly 80 generally includes two halves (not shown), which, when assembled about tube 160 (FIGS. 2 and 3), form a generally circular rotatable member 82. Rotatable assembly 80, or portions thereof, may be configured to house a drive assembly (not shown) and/or a knife assembly 180 (shown in FIG. 13), or components thereof. Examples of rotatable assembly embodiments, drive assembly embodiments, and knife assembly embodiments of the forceps 10 are described in the above-mentioned, commonly-assigned U.S. Pat. Nos. 7,150,097, 7,156,846, 7,597, 693 and 7,771,425.

Handle assembly 30 includes a fixed handle 50 and a movable handle 40. In some embodiments, the fixed handle 50 is integrally associated with the housing 20, and the handle 40 is selectively movable relative to the fixed handle 50. Movable handle 40 of the handle assembly 30 is ultimately connected to the drive assembly (not shown) and mechanically cooperate to impart movement of the jaw members 110 and 120 from an open position, wherein the jaw members 110 and 120 are disposed in spaced relation relative to one another, to a clamping or closed position, wherein the jaw members 110 and 120 cooperate to grasp tissue (e.g., 1420 shown in FIG. 14) therebetween. Examples of handle assembly embodiments of the forceps 10 are described in the above-mentioned, commonly-assigned U.S. Pat. Nos. 7,150,097, 7,156,846, 7,597,693 and 7,771,425.

Forceps 10 includes a switch 200 configured to permit the user to selectively activate the forceps 10 in a variety of different orientations, i.e., multi-oriented activation. As can be appreciated, this simplifies activation. When the switch 200 is depressed, electrosurgical energy is transferred through one or more leads (e.g., 311 shown in FIGS. 10, 12 and 13) to the jaw members 110 and 120. Switch 200 may be disposed on another part of the forceps 10 (e.g., the fixed handle 50, rotatable member 82, etc.) or another location on the housing assembly 20.

FIG. 4 shows a schematic of an end effector assembly 400 that includes an electrically-insulative hinge 450 according to an embodiment of the present disclosure. End effector assembly 400 (also referred to herein as a "jaw assembly") generally includes a pair of opposing jaw members 410 and 420. Jaw members 410 and 420 are pivotably mounted with respect to one another such that jaw member 410 pivots in a unilateral fashion from an open position to a closed position for grasping and manipulating tissue. Jaw members 410 and 420 shown in FIG. 4 are similar to the jaw members 110 and 120 of FIG. 1, respectively, and further description thereof is omitted in the interests of brevity.

As best shown in FIG. 7, the electrically-insulative hinge 450 is configured with one or more pivot-hole locators 454 to facilitate proper alignment of the jaw members 410 and 420 during assembly of the end effector assembly 400. Electrically-insulative hinge 450 is configured to electrically isolate the jaw members 410 and 420 from one another, and may be bonded or otherwise securely attached to either one of the jaw members. Electrically-insulative hinge 450 may be attached to the moveable jaw member 410 or the fixed jaw member 420 using any suitable material or bonding process.

Figure 5:
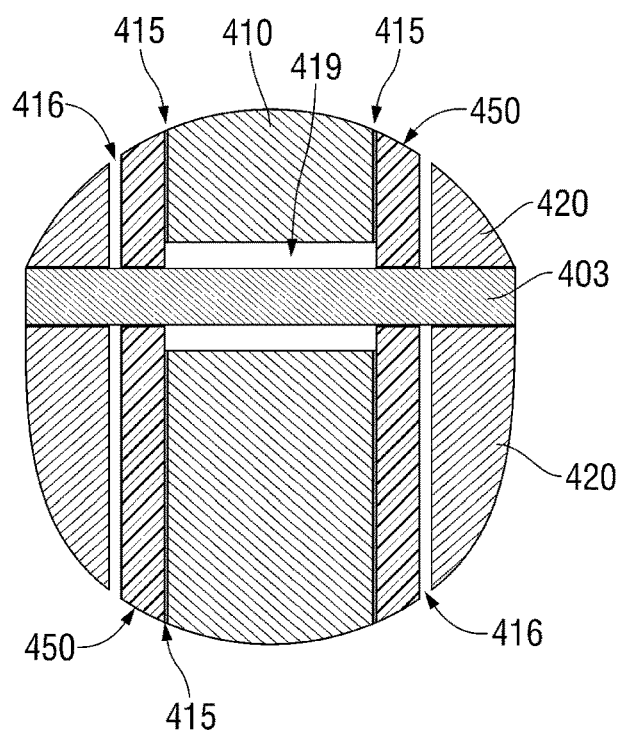
FIG. 5 is a cross-sectional view taken along the lines "I-I" of FIG. 4 illustrating the jaw members, pivot pin and electrically-insulative hinge according to an embodiment of the present disclosure.
Figure 6:
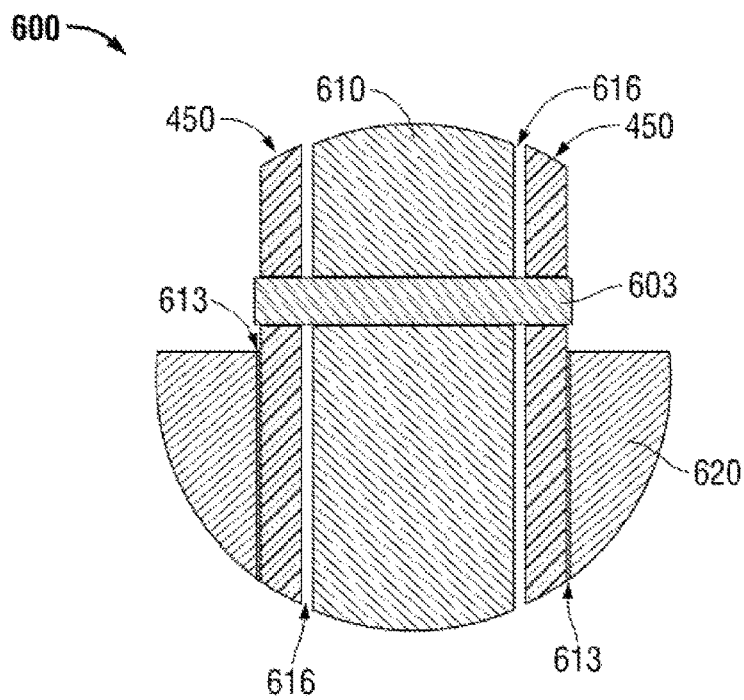
FIG. 6 is a cross-sectional view illustrating another embodiment of an end effector assembly including the electrically-insulative hinge of FIG. 4 in accordance with the present disclosure.

In the embodiment shown in FIGS. 4 and 5, the electrically-insulative hinge 450 is attached to the moveable jaw member 410, e.g., using an adhesive material 415. Alternatively, the electrically-insulative hinge 450 may be attached to the fixed jaw member (e.g., 620, as shown in FIG. 6). In some embodiments, as shown in FIG. 5, the fixed jaw member 420 and the electrically-insulative hinge 450 affixed to the moveable jaw member 410 are spaced apart by a gap 416, e.g., to reduce friction and/or wear.

During use of the jaw assembly 400, the electrically-insulative hinge 450 maintains electrical isolation of the jaw members 410 and 420, permitting energy potential to flow through the tissue being treated before returning through the opposing jaw. For example, when the jaw members 410 and 420 are electrically isolated from one another, electrosurgical energy can be effectively transferred through tissue 1420 to form seal 1450 as shown in FIG. 15.

In the embodiment shown in FIGS. 4 and 5, the unilateral jaw assembly 400 includes the electrically-insulative hinge 450 and a pivot pin 403 connecting the jaw members 410 and 420 at their rotation point, allowing the movable jaw member 410 to rotate relative to the fixed jaw member 420. As cooperatively shown in FIGS. 4 and 5, the pivot pin 403 passes through the pin slot or opening 419 defined in the moveable jaw member 410 and is received by the pivot holes defined in the fixed jaw member 420 (e.g., similar to the pivot holes 101*a*, 101*b* defined in the fixed jaw member 120 shown in FIG. 12) and the apertures 451 (FIG. 12) defined in the pivot-hole locators 454 of the electrically-insulative hinge 450 such that the jaw members 410 and 420 are pivotably mounted with respect to one another. Alternatively, wherein both jaw members are movable, a bilateral end effector assembly (e.g., bilateral end effector assembly 800 shown in FIG. 8) includes an electrically-insulative hinge (e.g., 850 shown in FIG. 8) configured to provide electrical isolation of the jaw members.

Figure 8:
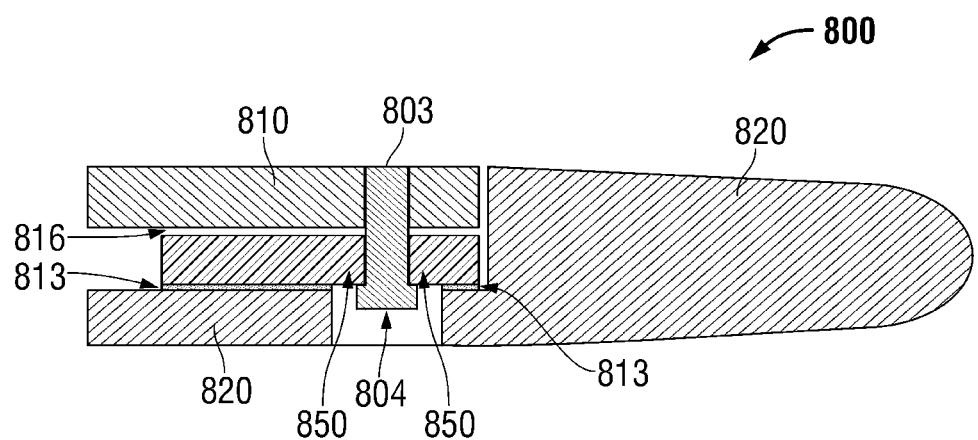
FIG. 8 is a schematic diagram of an embodiment of a bilateral end effector assembly with an electrically-insulative hinge in accordance with the present disclosure.

As shown in FIGS. 5, 6 and 8, the presently-disclosed jaw assemblies and electrically-insulative hinge embodiments allow a pivot pin (e.g., 403 shown in FIG. 5, 603 shown in FIG. 6, and 803 shown in FIG. 8) to be connected to one jaw member (e.g., 420 shown in FIG. 5, 610 shown in FIG. 6, and 810 shown in FIG. 8) and to the electrically-insulative hinge (e.g., 450 shown in FIGS. 5 and 6, and 850 shown in FIG. 8) that is bonded or otherwise attached to the opposing jaw member. In either unilateral or bilateral end effector embodiments, by connecting the pivot pin, which may be formed of an electrically-conductive material, to one jaw member and not to the other jaw member but, instead, to the electrically-insulative hinge, the pivot pin will not defeat the electrical isolation of the jaw members.

As cooperatively shown in FIGS. 4 and 7, electrically-insulative hinge 450 includes a generally U-shaped body member 452 and two end portions 453*a* and 453*b* disposed at the opposite ends of the body member 452. The shape and size of the body member 452 and end portions 453*a* and 453*b*, which are described in more detail below, may be varied from the configuration depicted in FIGS. 4 through 7.

Electrically-insulative hinge 450 is configured with one or more pivot-hole locators 454, e.g., defined by the end portions 453*a* and/or 453*b*. In some embodiments, each of the end portions 453*a* and 453*b* includes an aperture 451 defined therein. Alternatively, only one of the end portions 453a or 453b includes an aperture 451 defined therein. Aperture 451 is configured to receive a portion of a pivot pin 403 therein. Electrically-insulative hinge 450 is formed from a suitable electrically-insulative material. Examples of electrically-insulative materials that may be suitable for forming the electrically-insulative hinge 450 include without limitation plastics, ceramic, glass or other non-conductive materials with desired properties. Electrically-insulative hinge 450 may be fastened to either one of the jaws by any suitable process including without limitation adhesive bonding, soldering, brazing, overmolding, mechanical interlock, snaps, bent tabs, screws or other mechanical fasteners, etc.

FIG. 6 shows a unilateral jaw assembly 600 that includes the electrically-insulative hinge 450, a pivot pin 603, and jaw members 610 and 620. In the embodiment shown in FIG. 6, the electrically-insulative hinge 450 is attached to the fixed jaw member 620, e.g., using an adhesive material 613. In some embodiments, the moveable jaw member 610 and the electrically-insulative hinge 450 that is attached to the fixed jaw member 620 are spaced apart by a gap 616, e.g., to reduce friction and/or wear.

FIG. 7 shows a schematic of a fixture 780 configured to releaseably hold the end effector assembly 600 of FIG. 6, such as during a fastening process, according to an embodiment of the present disclosure. Fixture 780 is configured to hold the jaw members 610 and 620 in proper alignment while the electrically-insulative hinge 450 is fastened and/or cured to the moveable jaw member 610 or the fixed jaw member 620. In some embodiments, the jaw members 610 and 620 are self-aligned by pre-assembling the jaw components including the jaw members 610 and 620, the electrically-insulative hinge 450 and the pivot pin 603. Any remaining degrees of freedom are then constrained by the holding fixture 780 until the bond between the electrically-insulative hinge 450 and the fixed jaw member 620 (shown in FIG. 6) or the bond between the electrically-insulative hinge 450 and the moveable jaw member 610 is completed. In the embodiment shown in FIG. 7, the fixture 780 serves to hold the sealing surface of the jaw member 610 directly against the sealing surface of the jaw member 620 with desired jaw gap controlled by gap features on the jaw members 610, 620 and/or with shims used during assembly, which may be a critical alignment, while the bond is made. When the bonding process is completed, the holding fixture 780 may be removed from the jaw assembly 600. It will be appreciated that additional manufacturing steps may be undertaken after the bonding process is completed, prior to the release of the jaw assembly 600 from the fixture 780. In some embodiments, after the bonding process is completed, the pivot pin 603 may be removed and the jaws separated, if desired, for assembly or further processing.

In some embodiments, the fixture 780 includes a shaft 782, a first leg member 783 disposed at a first end 781a of the shaft 782, and a second leg member 785 disposed at a second end 781b of the shaft 782. First leg member 783 and the second leg member 785 may extend in a substantially perpendicular direction away from the shaft 782, such that the fixture 780 may have a generally U-like shape. In some embodiments, the shaft 782, the first leg member 783 and the second leg member 785 are integrally formed. In some embodiments, the first leg member 783 includes a first tip portion 784 and the second leg member 785 includes a second tip portion 786. In some embodiments, the shaft 782, the first leg member 783, the first tip portion 784, the second leg member 785 and the second tip portion 786 may be configured such that the fixture 780 has a generally C-like shape. Fixture 780 could be formed in a variety of shapes suitable to constrain the jaw members adequately during completion of the bonding process. Fixture 780 may be made from metal, plastic, ceramic and/or other suitable materials with desired properties, e.g., machinability, flexibility, moldability, temperature resistance, chemical resistance, etc. Fixture 780 and/or the jaw members may include features to enable quick, accurate, secure and reliable holding, including without limitation flats, slots, holes, grooves, recesses, pins, stops or any other suitable features that provides alignment and/or mating engagement of the fixture 780 to the jaw members. In some embodiments, either one (or both) of the jaw members may include one or more grooves or recesses defined therein configured and disposed to accept or matingly engage with one or more edge portions or protrusions formed on the first tip portion 784 and/or the second tip portion 786 of the fixture 780.

Figure 9:
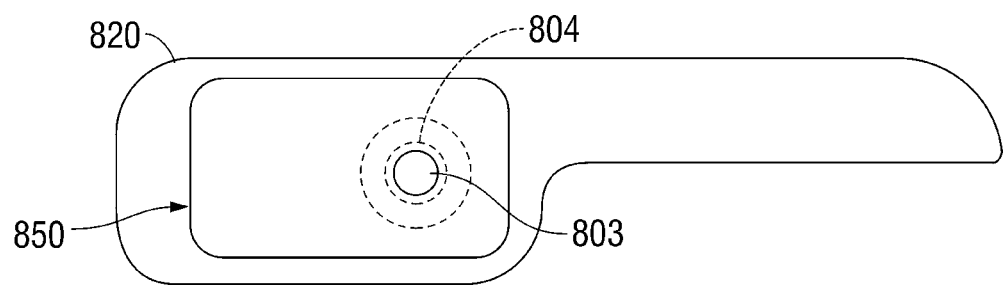
FIG. 9 is a side-view schematic diagram of the end effector assembly of FIG. 8 illustrating the upper jaw member, pivot pin and electrically-insulative hinge according to an embodiment of the present disclosure.

FIG. 8 shows a bilateral end effector assembly 800 that includes an electrically-insulative hinge 850 that is configured to provide electrical isolation of the first and second jaw members 810 and 820. Electrically-insulative hinge 850 is formed from a suitable electrically-insulative material, and includes an aperture defined therein. FIG. 9 is a side-view of the end effector assembly 800 illustrating the second jaw member 820, pivot pin 803, and electrically-insulative hinge 850.

In the embodiment shown in FIGS. 8 and 9, the electrically-insulative hinge 850 is bonded or otherwise securely attached to the second jaw member 820, e.g., using an adhesive material 813. Alternatively, the electrically-insulative hinge 850 may be attached to the first jaw member 810. Electrically-insulative hinge 850 may be attached to the first jaw member 810 or the second jaw member 820 using any suitable material or bonding process.

As shown in FIG. 8, the pivot pin 803 is received by an aperture defined in the electrically-insulative hinge 850 and a pivot hole defined in the first jaw member 810. In some embodiments, the pivot pin 803 is secured by a fastener 804, e.g., a pin, cap, shoulder, rivet, swage, nut, etc. In some embodiments, the first jaw member 810 and the electrically-insulative hinge 850 that is attached to the second jaw member 820 are spaced apart by a gap 816, e.g., to reduce friction and thereby minimize wear.

Figure 10:
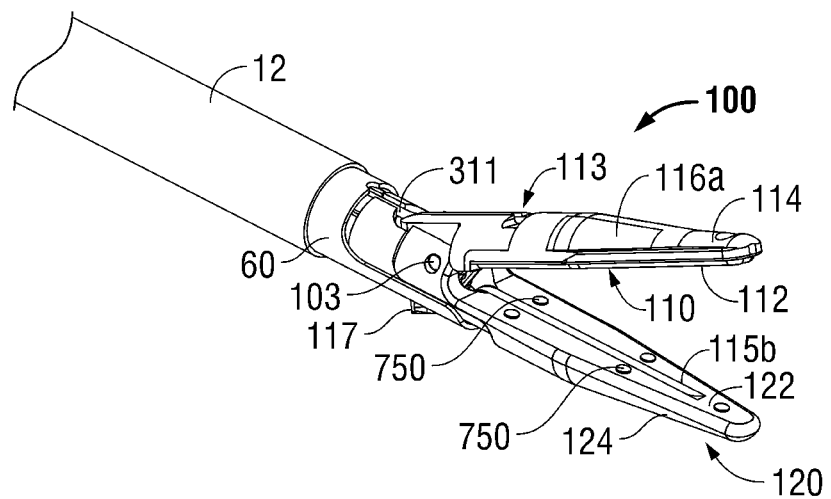
FIG. 10 is an enlarged, left perspective view of the end effector assembly of FIG. 1 shown with the jaw members in an open configuration according to an embodiment of the present disclosure.
Figure 12:
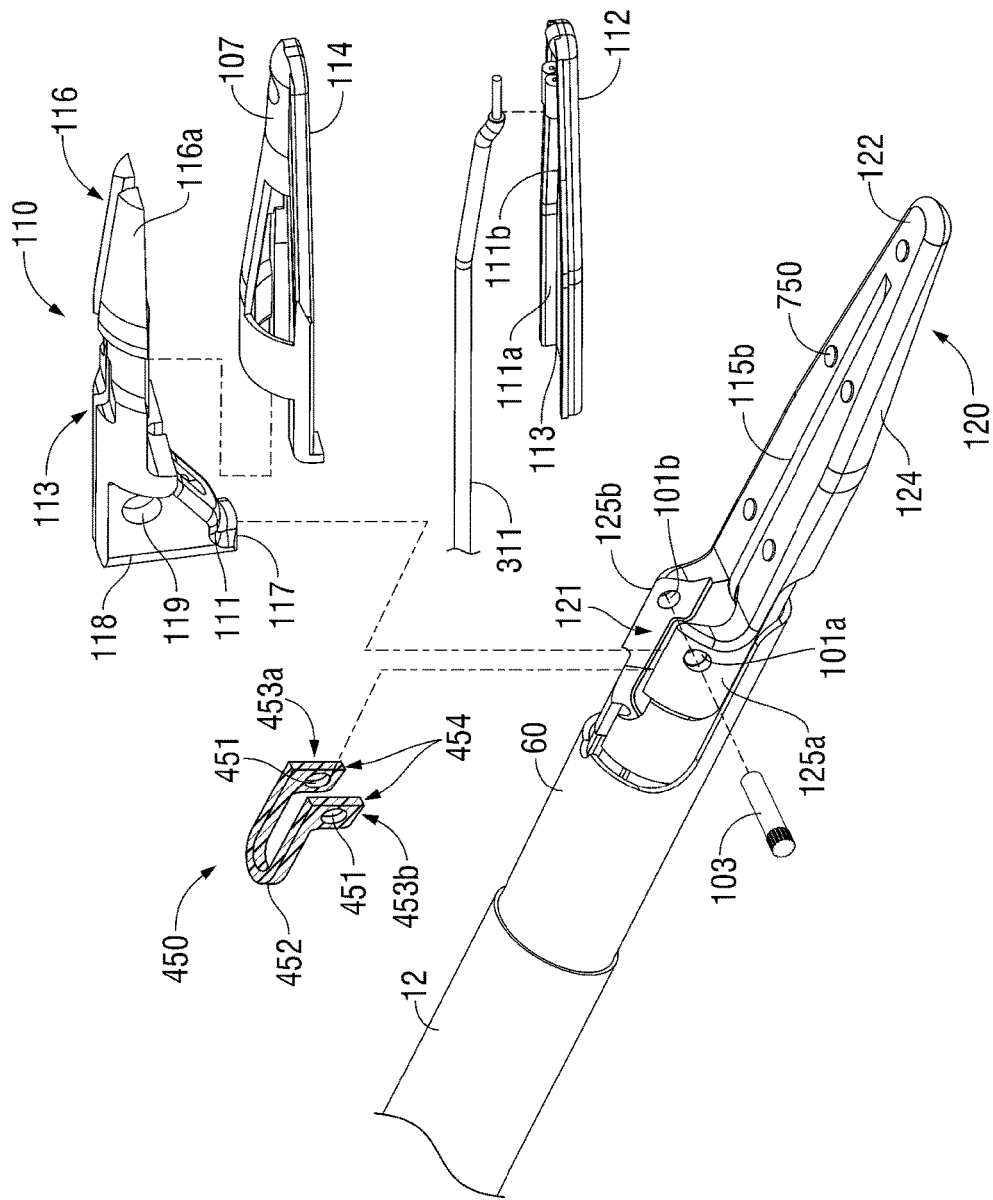
FIG. 12 is an enlarged, top, left perspective view of the end effector assembly of FIG. 1 with parts separated according to an embodiment of the present disclosure.
Figure 13:
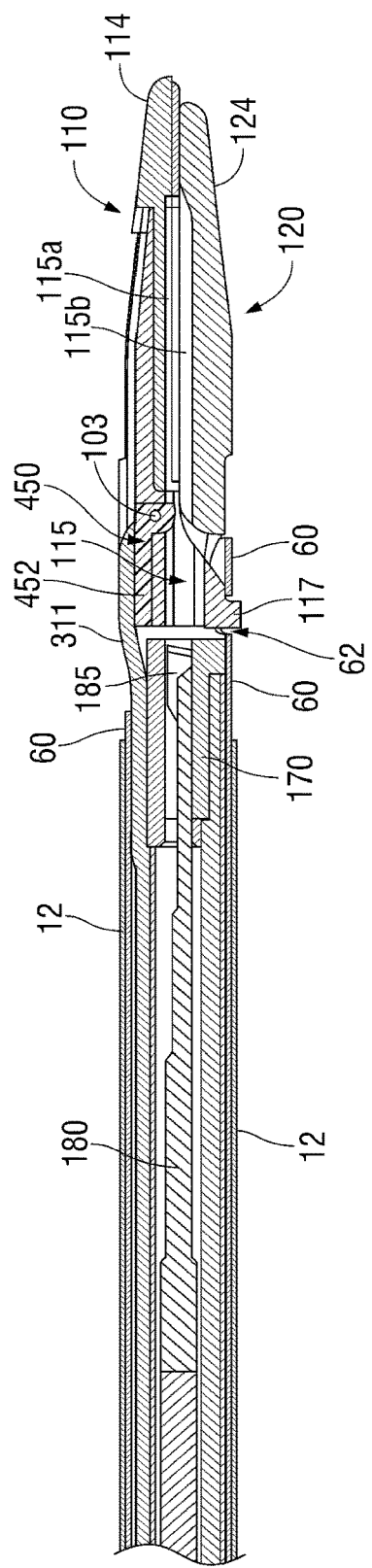
FIG. 13 is an enlarged, cross-sectional view of a portion of the forceps shown in FIG. 1 according to an embodiment of the present disclosure.

As shown in FIGS. 10 and 12, jaw member 110 also includes a jaw housing 116 that includes an insulative substrate or insulator 114 and an electrically-conductive surface 112. Insulator 114 is configured to securely engage the electrically-conductive sealing surface 112. This may be accomplished by stamping, by overmolding, by overmolding a stamped electrically-conductive sealing plate and/or by overmolding a metal injection molded seal plate. For example and as shown in FIG. 12, the electrically-conductive sealing plate 112 includes a series of upwardly extending flanges 111a and 111b that are designed to matingly engage the insulator 114. Insulator 114 includes a shoe-like interface 107 disposed at a distal end thereof which is configured to engage the outer periphery 116a of the housing 116 in a slip-fit manner. The shoe-like interface 107 may also be overmolded about the outer periphery of the jaw 110 during a manufacturing step. Lead 311 terminates within the shoe-like interface 107 at the point where the lead 311 electrically connects to the sealing plate 112. The movable jaw member 110 is configured with a wire channel 113 to guide the cable lead 311 into electrical continuity with the sealing plate 112.

As best shown in the exploded view of FIG. 12, jaw members 110 and 120 are pivotably mounted with respect to one another such that the jaw member 110 pivots in a unilateral fashion from a first open position to a second closed position for grasping and manipulating tissue 1420 (shown in FIG. 14). Fixed jaw member 120 includes a pair of proximal, upwardly extending flanges 125a and 125b that define a cavity 121 configured to receive the pivot flange 118 of the movable jaw member 110 therein. Each of the flanges 125a and 125b includes an aperture 101a and 101b, respectively, defined therethrough that secures the pivot pin 103 on opposite sides of a pin slot or opening 119 disposed within the jaw member 110.

Jaw member 110 includes a pivot flange 118. Protrusion 117 extends from the pivot flange 118 and includes an arcuately-shaped inner surface 111 configured to matingly engage the aperture 62 of sleeve 60 upon retraction thereof. Pivot flange 118 includes an opening 119 defined therein that is configured to allow the pivot pin 103 to pass therethrough, e.g., to allow jaw member 110 to rotate relative to jaw member 120 upon retraction of the reciprocating sleeve 60. In some embodiments, the pivot pin 103 mounts to the electrically-insulative hinge 450 through a pair of apertures 451 defined therein and mounts to the stationary jaw member 120 through a pair of apertures 101a and 101b disposed within a proximal portion of the jaw member 120.

Jaw member 120 fixes to the end of a rotatable tube 160 (shown in FIGS. 2 and 3) which is part of the rotatable assembly 80 such that rotation of the tube 160 will impart rotation to the end effector assembly 100. As shown in FIG. 2, the distal end of the tube 160 is generally C-shaped to include two upwardly extending flanges 162a and 162b that define a cavity 165 for receiving the proximal end of the fixed jaw member 120 inclusive of C-shaped cuff 170 and slide pin 171. The tube cavity 165 retains and secures the jaw member 120 in a friction-fit manner; however, the jaw member 120 may be welded to the tube 160 depending upon a particular purpose. Tube 160 also includes an inner cavity 169 (shown in FIG. 3) defined therethrough that reciprocates the knife assembly 180 upon distal activation thereof and an elongated guide rail 163 that guides the knife assembly 140 during distal activation. The proximal end of tube 160 includes a laterally-oriented slot 168 that is designed to interface with the rotating assembly 80, as described in the above-mentioned, commonly-assigned U.S. Pat. Nos. 7,150, 097, 7,156,846, 7,597,693 and 7,771,425.

Jaw member 120 includes a rear C-shaped cuff 170 having a slot 177 defined therein which is configured to receive a slide pin 171. Slide pin 171 includes a slide rail 176 that extends substantially the length thereof, configured to slide into friction-fit engagement within slot 177. A pair of chamfered plates 172a and 172b extends generally radially from the slide rail 176 and include a radius that is substantially the same radius as the outer periphery of the rotatable tube 160 such that the shaft 12 can encompass each of the same upon assembly. The chamfered plates 172a and 172b also form a wire channel 175 that is configured to guide the cable lead 311 from the tube 160 and into the movable jaw member 110 (see FIG. 12). Lead 311 carries a first electrical potential to movable jaw 110. The electrically-conductive surface 112 and the insulator 114, when assembled, include a longitudinally-oriented channel 115a defined therethrough for reciprocation of the knife blade 185.

Jaw member 120 includes similar elements to jaw member 110 such as jaw housing 126 having an insulator 124 and an electrically-conductive sealing surface 122 that is configured to securely engage the insulator 124. Likewise, the electrically-conductive surface 122 and the insulator 124, when assembled, include a longitudinally-oriented channel 115b defined therethrough for reciprocation of the knife blade 185. Knife channel 115 (made up of half channels 115a and 115b) is blocked when the jaws members 110 and 120 are opened and aligned for distal activation when the jaw members 110 and 120 are closed.

Jaw member 120 is connected to a second electrical potential through tube 160 which is connected at its proximal end to a lead (not shown). Fixed jaw 120 may include a fuse clip, spring clip or other electro-mechanical connection. In some embodiments, at least one jaw member, e.g., 120, includes a stop member 750 that limits the movement of the two opposing jaw members 110 and 120 relative to one another. Stop member embodiments and internal electrical connections of the forceps 10 are described in the above-mentioned, commonly-assigned U.S. Pat. Nos. 7,150, 097, 7,156,846, 7,597,693 and 7,771,425. As best shown in FIG. 2, the rotatable tube 160 includes an elongated guide slot 167 disposed in an upper portion thereof and configured to carry lead 311 therealong.

Proximal movement of the tube 60 engages detent 117 to pivot the jaw member 110 to a closed position. It is understood from FIG. 12 that the jaw member 120 is stationary.

FIG. 14 shows the end effector assembly 100 of FIG. 1 shown grasping tissue 1420. In some embodiments, the end effector assembly 100 may include a gap distance "G" between opposing sealing surfaces 112 during sealing, e.g., in the range from about 0.001 inches to about 0.006 inches. In some embodiments, the end effector assembly 100 includes a gap distance "G" between opposing sealing surfaces 112 during sealing that ranges from about 0.002 to about 0.003 inches. As shown in FIG. 16, the forceps 10 is insertable through a cannula 500 into a patient's body for use during a procedure.

As energy is being selectively transferred to the end effector assembly 100, across the jaw members 110 and 120 and through the tissue 1420, a tissue seal 1450 forms isolating two tissue halves 1420a and 1420b (see FIG. 15). The knife assembly 180 which, when activated via the trigger assembly 70, progressively and selectively divides the tissue 1420 along a tissue plane in a precise manner to divide the tissue 1420 into two sealed halves (not shown). Once the tissue 1420 is divided into tissue halves, the jaw members 110 and 120 may be opened by re-initiation or re-grasping of the handle 40.

Hereinafter, methods of manufacturing an end effector assembly are described with reference to FIGS. 17 through 19. It is to be understood that the steps of the methods provided herein may be performed in combination and in a different order than presented herein without departing from the scope of the disclosure.

Figure 17:
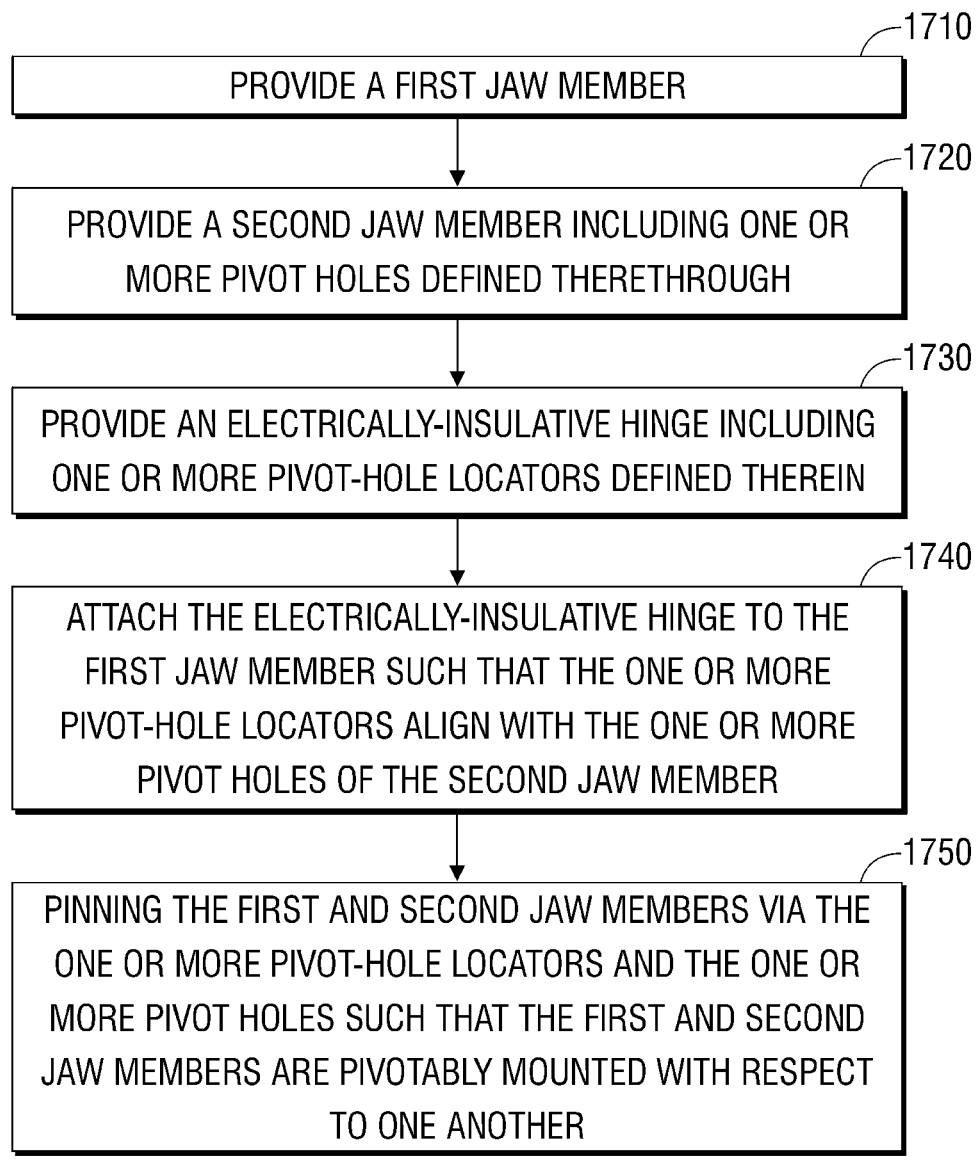
FIG. 17 is a flowchart illustrating a method of manufacturing an end effector assembly according to an embodiment of the present disclosure.

FIG. 17 is a flowchart illustrating a method of manufacturing an end effector assembly 100 according to an embodiment of the present disclosure that includes a first jaw member 110 and a second jaw member 120. In some embodiments, the first and second jaw members 110, 120 are configured to be pivotably mounted with respect to one another.

In step 1710, a first jaw member 110 is provided. The first jaw member 110 includes a pin slot or opening 119 defined therethrough.

In step 1720, a second jaw member 120 is provided. The second jaw member 120 includes one or more pivot holes 101a, 101b defined therethrough.

In step 1730, an electrically-insulative hinge 450 is provided that is configured to electrically isolate the jaw members from one another. The electrically-insulative hinge 450 is formed from a suitable electrically-insulative material.

The electrically-insulative hinge 450 includes one or more pivot-hole locators 454 defined therein, and may take any suitable shape.

In some embodiments, the electrically-insulative hinge 450 includes a generally U-shaped body member 452 and two end portions 453a, 453b disposed at the opposite ends of the body member 452. One or more of the end portions 453a, 453b includes an aperture 451 defined therein configured to receive a portion of a pivot pin 103 therein. In some embodiments the one or more pivot-hole locators 454 are defined by the one or more end portions 453a, 453b that include the aperture 451.

In step 1740, the electrically-insulative hinge 450 is attached to the first jaw member 110 such that the one or more pivot-hole locators 454 align with the one or more pivot holes 101a, 101b of the second jaw member 120. The electrically-insulative hinge 450 may be bonded or otherwise securely attached the first jaw member 110 using any suitable material or bonding process, e.g., adhesive bonding, soldering, brazing, overmolding, mechanical interlock, snaps, bent tabs, etc.

In step 1750, the first and second jaw members 110, 120 are pinned via the one or more pivot-hole locators 454 and the one or more pivot holes 101a, 101b such that the first and second jaw members 110, 120 are pivotably mounted with respect to one another.

Figure 18:
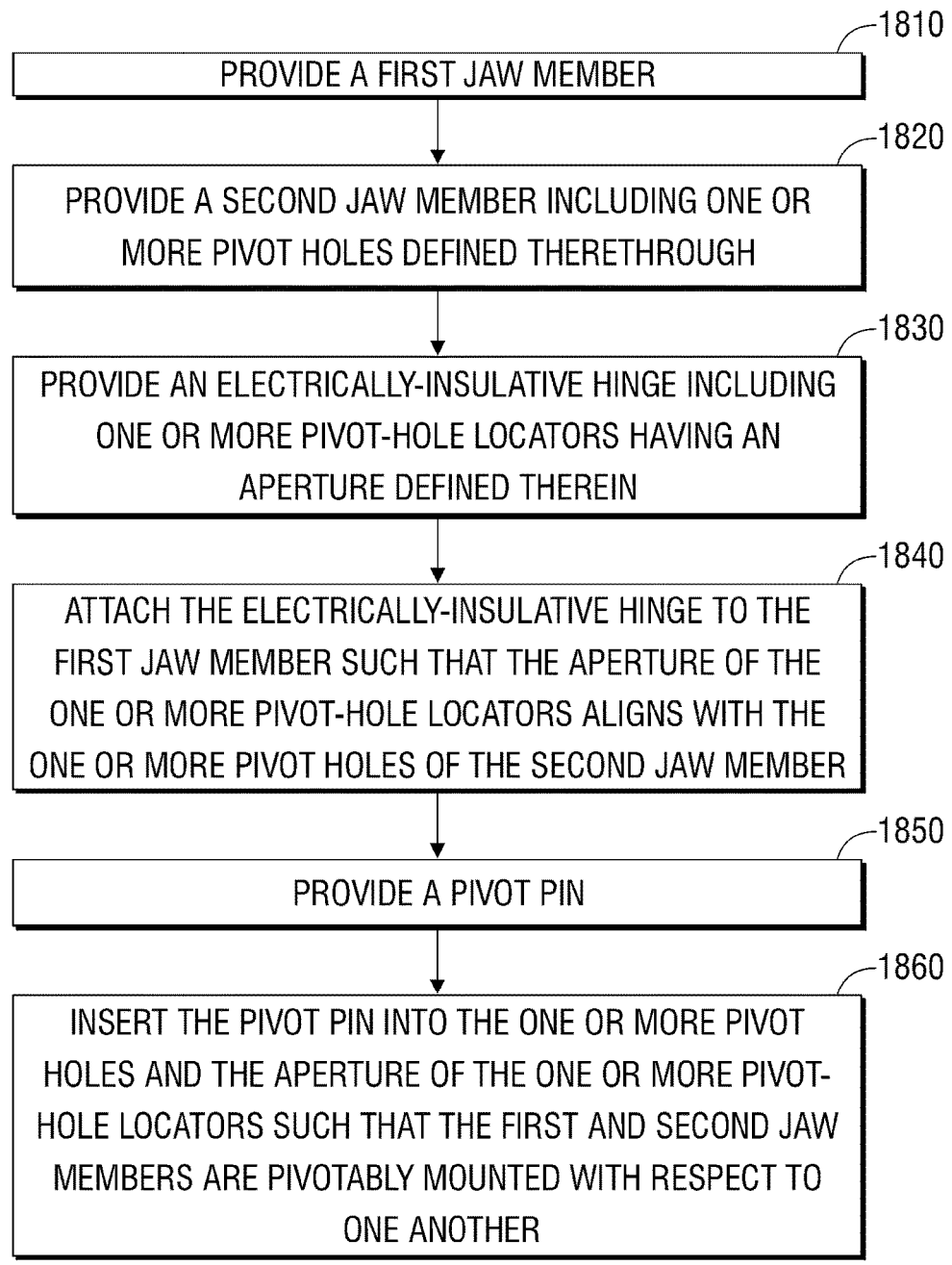
FIG. 18 is a flowchart illustrating a method of manufacturing an end effector assembly according to another embodiment of the present disclosure.

FIG. 18 is a flowchart illustrating a method of manufacturing an end effector assembly 100 according to an embodiment of the present disclosure. In step 1810, a first jaw member 110 is provided. The first jaw member 110 includes a pin slot or opening 119 defined therethrough.

In step 1820, a second jaw member 120 is provided. The second jaw member 120 includes one or more pivot holes 101a, 101b defined therethrough.

In step 1830, an electrically-insulative hinge 450 is provided that is configured to electrically isolate the jaw members from one another. The electrically-insulative hinge 450 includes one or more pivot-hole locators 454 having an aperture 451 defined therein.

In step 1840, the electrically-insulative hinge 450 is attached to the first jaw member 110 such that the aperture 451 of the one or more pivot-hole locators 454 aligns with the one or more pivot holes 101a, 101b of the second jaw member 120. The electrically-insulative hinge 450 may be bonded or otherwise securely attached the first jaw member 110 using any suitable material or bonding process.

In step 1850, a pivot pin 103 is provided. The pivot pin 103 is configured to pass through the pin slot or opening 119 and to be received by the one or more pivot holes 101a, 101b.

In step 1860, the pivot pin 103 is inserted into the one or more pivot holes 101a, 101b and the aperture 451 of the one or more pivot-hole locators 454 such that the first and second jaw members 110, 120 are pivotably mounted with respect to one another.

Figure 19:
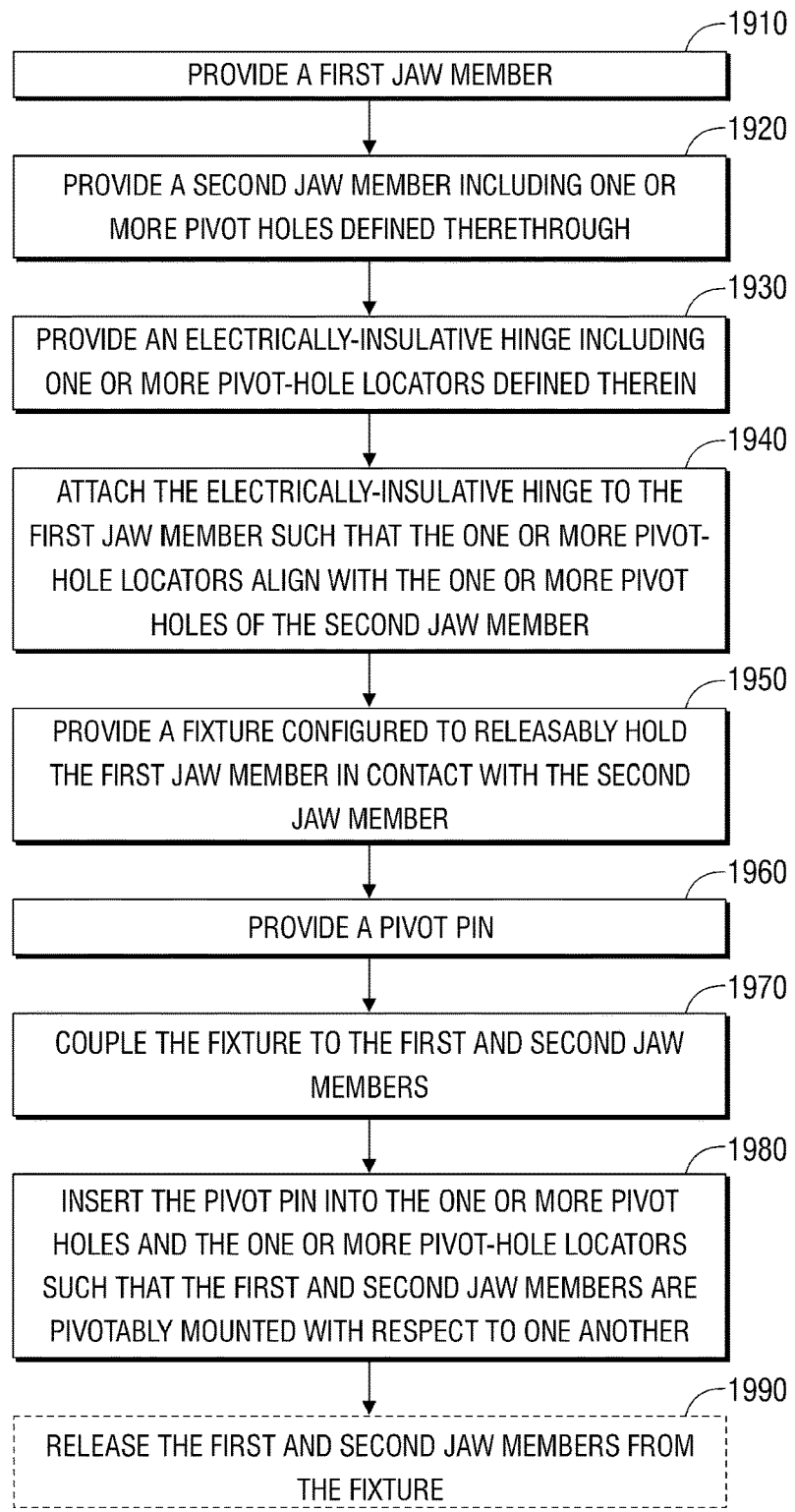
FIG. 19 is a flowchart illustrating a method of manufacturing an end effector assembly according to yet another embodiment of the present disclosure.

FIG. 19 is a flowchart illustrating a method of manufacturing an end effector assembly 100 according to an embodiment of the present disclosure. In step 1910, a first jaw member 110 is provided. The first jaw member 110 includes a pin slot or opening 119 defined therethrough.

In step 1920, a second jaw member 120 is provided. The second jaw member 120 includes one or more pivot holes 101a, 101b defined therethrough.

In step 1930, an electrically-insulative hinge 450 is provided that is configured to electrically isolate the jaw members from one another. The electrically-insulative hinge 450 includes one or more pivot-hole locators 454 defined therein.

In step 1940, the electrically-insulative hinge 450 is attached to the first jaw member 110 such that the one or more pivot-hole locators 454 align with the one or more pivot holes 101a, 101b of the second jaw member 120. The electrically-insulative hinge 450 may be bonded or otherwise securely attached the first jaw member 110 using any suitable material or bonding process.

In step 1950, a holding fixture 780 is provided. The fixture 780 is configured to releaseably hold the first jaw member 110 in contact with the second jaw member 120. In some embodiments, the fixture 780 is configured to hold the first and second jaw members 110, 120 in proper alignment while the electrically-insulative hinge 450 is fastened and/or cured to the first jaw member 110 (or the second jaw member 120). In some embodiments, the fixture 780 is configured to hold the sealing surface 112 of the first jaw member 110 directly against the sealing surface 122 of the second jaw member 120 in proper alignment while the electrically-insulative hinge 450 is fastened and/or cured to the first jaw member 110 (or the second jaw member 120).

In step 1960, a pivot pin 103 is provided. In some embodiments, the pivot pin 103 is configured to pass through the pin slot or opening 119 and to be received by the one or more pivot holes 101a, 101b.

In step 1970, the fixture 780 is releasably coupled to the first and second jaw members 110, 120. In some embodiments, the jaw member 110 and/or the jaw member 120 may include one or more grooves or recesses defined therein configured and disposed to accept or matingly engage with one or more edge portions or protrusions formed on a first and tip portion 784 and/or a second tip portion 786 of the fixture 780.

In step 1980, the pivot pin 103 is inserted into the one or more pivot holes 101a, 101b and the one or more pivot-hole locators 454 such that the first and second jaw members 110, 120 are pivotably mounted with respect to one another.

In some embodiments, after the pivot pin 103 is inserted into the one or more pivot holes 101a, 101b and the one or more pivot-hole locators 454, in step 1980, and after the bond between the electrically-insulative hinge 450 and the first jaw member 110 is completed, the first and second jaw members 110, 120 are released from the fixture 780, in step 1990. It will be appreciated that additional manufacturing steps may be undertaken after the step 1980, prior to the release of the first and second jaw members 110, 120 from the fixture 780.

The presently-disclosed bipolar forceps is capable of directing energy into tissue, and may be suitable for use in a variety of procedures and operations. The above-described bipolar forceps embodiments may utilize both mechanical clamping action and electrical energy to effect hemostasis by heating tissue and blood vessels to coagulate, cauterize, cut and/or seal tissue. The jaw assemblies may be either unilateral or bilateral. The above-described bipolar forceps embodiments may be suitable for utilization with endoscopic surgical procedures and/or hand-assisted, endoscopic and laparoscopic surgical procedures. The above-described bipolar forceps embodiments may be suitable for utilization in open surgical applications.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An end effector assembly for a forceps, the end effector assembly comprising:
    a first jaw member including a first pivot pin opening defined therein and having a first sealing surface;
    a second jaw member including a second pivot pin opening defined therein and having a second sealing surface opposing the first sealing surface;
    a pivot pin configured to pass through the first and second pivot pin openings to pivotably couple the first and second jaw members to one another about the pivot pin; and
    a hinge positioned between the first jaw member and the second jaw member configured to electrically isolate the first and second jaw members from one another, the hinge including a U-shaped body disposed in a plane parallel to at least one of the first and second sealing surfaces and including first and second end portions disposed at opposite ends of the U-shaped body, the first and second end portions each defining a pivot hole that receives the pivot pin.

2. The end effector assembly according to claim 1, wherein the pivot pin is formed of an electrically conductive material, and wherein the hinge electrically isolates the pivot pin from at least one of the first and second jaw members.

3. The end effector assembly according to claim 1, wherein the hinge is fastened to the second jaw member.

4. The end effector assembly according to claim 3, wherein the hinge is fastened to the second jaw member by at least one of adhesive bonding, soldering, brazing, overmolding, mechanically interlocking, snapping, screwing, or bending of tabs.

5. The end effector assembly according to claim 3, wherein the pivot holes of the first and second end portions are aligned with and disposed on opposite sides of the second pivot pin opening, the pivot pin passing through the pivot holes of the first and second end portions.

6. The end effector assembly according to claim 5, wherein the pivot holes each have a first diameter and the second pivot pin opening has a second diameter larger than the first diameter.

7. The end effector assembly according to claim 5, wherein the pivot pin is fixed within the first pivot pin opening of the first jaw member.

8. The end effector assembly according to claim 1, wherein the pivot pin defines a pivot axis transverse to a longitudinal axis of the first jaw member and a longitudinal axis of the second jaw member.

9. The end effector assembly according to claim 1, wherein the U-shaped body has a proximal backspan, a first leg extending distally from a first end of the backspan to the first end portion, and a second leg extending from a second end of the backspan to the second end portion.

10. The end effector assembly according to claim 9, wherein the backspan, the first leg, and the second leg have a first dimension defined orthogonal to the plane parallel to the at least one of the first and second sealing surfaces, wherein each of the first and second end portions have a second dimension defined orthogonal to the plane parallel to the at least one of the first and second sealing surfaces, and wherein the second dimension is greater than the first dimension.

11. The end effector assembly according to claim 9, wherein the first end portion extends from the first leg in a direction towards and orthogonal to the first and second sealing surfaces, and wherein the second end portion extends from the second leg in a direction towards and orthogonal to the first and second sealing surfaces.

12. The end effector assembly according to claim 1, wherein the first jaw member includes a pair of proximal flanges that define a cavity therebetween, wherein the second jaw member includes a pivot flange received within the cavity, and wherein each proximal flange defines a portion of the first pivot pin opening.

13. The end effector assembly according to claim 12, wherein the first and second end portions are disposed on opposite sides of the pivot flange and are each disposed between the pivot flange of the second jaw member and one of the pair of proximal flanges of the first jaw member.

14. The end effector assembly according to claim 13, wherein the hinge is disposed about a proximal surface of the pivot flange.

15. An end effector assembly for a forceps, the end effector assembly comprising:
    a first jaw member having a pair of proximal flanges defining a cavity therebetween, each proximal flange including a pivot pin opening defined therein;
    a second jaw member having a proximal pivot flange including a pivot pin opening defined therein, the pivot flange positioned within the cavity of the first jaw member;
    a pivot pin configured to pass through the pivot pin openings of the first and second jaw members to pivotably couple the first and second jaw members to one another about the pivot pin; and
    a hinge positioned between the first jaw member and the second jaw member configured to electrically isolate the first and second jaw members from one another, the hinge having a U-shaped body including first and second end portions disposed at opposite ends of the U-shaped body, the first and second end portions each defining a pivot hole that receives the pivot pin.

16. The end effector assembly according to claim 15, wherein the pivot holes each have a first diameter and the pivot pin opening of the second jaw member has a second diameter larger than the first diameter.

17. The end effector assembly according to claim 15, wherein the pivot pin is fixed within the pivot pin opening of the first jaw member.

18. The end effector assembly according to claim 15, wherein the hinge is disposed about a proximal surface of the pivot flange.

19. A forceps, comprising:
    a housing;
    a shaft extending from the housing and including a distal end; and
    an end effector assembly supported at the distal end of the shaft, the end effector assembly including:
        a first jaw member including a first pivot pin opening defined therein and having a first sealing surface;
        a second jaw member including a second pivot pin opening defined therein and having a second sealing surface opposing the first sealing surface;
        a pivot pin configured to pass through the first and second pivot pin openings to pivotably couple the first and second jaw members to one another about the pivot pin; and
        a hinge positioned between the first jaw member and the second jaw member configured to electrically isolate the first and second jaw members from one another, the hinge including a U-shaped body disposed in a plane parallel to at least one of the first and second sealing surfaces and including first and second end portions disposed at opposite ends of the U-shaped body, the first and second end portions each defining a pivot hole that receives the pivot pin.

20. The forceps according to claim 19, wherein the first jaw member is fixed to the distal end of the shaft.

* * * * *